US006049615A

United States Patent [19]

Chou et al.

[11] Patent Number: 6,049,615

[45] Date of Patent: Apr. 11, 2000

[54] INTERGRATED ACTIVE NOISE CONTROL SYSTEM FOR AIR HANDLING UNIT

[75] Inventors: Shau-Tak R. Chou, Liverpool; Mark A. Daniels, Manlius, both of N.Y.; Duane C. McCormick, Colchester, Conn.

[73] Assignee: Carrier Corporation, Syracuse, N.Y.

[21] Appl. No.: 08/884,231

[22] Filed: Jun. 27, 1997

[51] Int. Cl.$^{7}$ ........ A61F 11/06

[52] U.S. Cl. ........ 381/71.3; 381/336

[58] Field of Search ........ 381/91, 71.1, 71.2, 381/71.3, 71.4, 71.5, 71.7, 336, 337; 415/119; 181/0.5, 198

[56] References Cited

U.S. PATENT DOCUMENTS 5,499,423 3/1996 Joo et al. ........ 381/71.3

FOREIGN PATENT DOCUMENTS 2-61450 1/1990 Japan .

*Primary Examiner*—Vivian Chang

[57] ABSTRACT

The internal fan arrangement of an AHU is reconfigured by discharging directly from the scroll into a 90° elbow. The bend of the elbow defines a converging section terminating in a throat which leads to a diverging section. Additionally, the ANC structure is located in the elbow with the noise sensing microphones being located at or near the fan outlet.

16 Claims, 4 Drawing Sheets

INTERGRATED ACTIVE NOISE CONTROL SYSTEM FOR AIR HANDLING UNIT

BACKGROUND OF THE INVENTION

In multi-story buildings such as office buildings, hotels, apartment buildings, etc. a machinery room is normally located on each floor. Since the space occupied by the machinery room represents space unavailable for renting, it is desirable to minimize such space. Because the machinery room usually backs on the elevators, the space required by the elevators can dictate one of the dimensions of the machinery room and the space between floors dictates a second dimension. The air handling unit (AHU) for circulating conditioned air throughout a floor is located in the machinery room on that floor. The noise from the air handling unit, particularly at low frequency, has A become a major concern for building occupants in recent years due to its impact on room sound quality.

To control the noise from AHUs, duct active noise control (ANC) systems are starting to be employed in air distribution systems. An ANC system basically requires the sensing of the noise associated with the fan for distributing the air, producing a noise canceling signal and determining the results of the canceling signal so as to provide a correction signal to the loudspeaker. There is a time delay associated with sensing the noise and producing a canceling signal. This time delay necessary for the canceling to take place equates to the distance in the system required between the reference, or input, noise sensor and the loudspeaker. Additional space is required between the loudspeaker and the error sensor which also equates to a distance in the system. The space limitations in existing buildings severely limits the retrofitting or replacement of existing equipment with equipment using conventional ANC approaches. In new buildings the extra space required by conventional ANC approaches comes at a high price in the reduced rentable space which would result on each floor.

Other than the additional space requirements associated with duct ANC systems, there are conventional design approaches associated with fans that preclude significantly reducing the size of the fan and the fan discharge. Specifically, in conventional ANC designs a further problem is that the input noise sensing microphone cannot be located near the fan discharge where a high level of turbulence prevents accurate sound measurement and thereby compromises noise cancellation. To offset this problem, designers are forced to place the noise sensing microphone far from the discharge, for example three times the blower diameter downstream, so that flow leaving the blower discharge can fully occupy the duct and hence lower the level of turbulence. In the case of top discharge units, a large elbow transition would also be required.

SUMMARY OF THE INVENTION

At the outlet of the scroll of a blower defined by the cutoff, a 90° elbow is located. The elbow is made up of a bend portion located between two leg portions and has an inlet corresponding to the outlet defined at the cutoff and defines a portion of the air distribution duct. Since the cross sectional area of the discharge flow path is reduced, as compared to convention designs, a tighter elbow is possible which contributes to a more compact design. To ensure that a proper acoustic path is followed by sound from the blower, the cross sectional area is further reduced in the bend which permits an even tighter elbow and an even more compact design. A conventional expansion of the flow takes place downstream of the bend in the elbow, in the downstream leg, which follows a diverging shape. Additionally, the ANC structure is incorporated into the inlet of the bend in the elbow and down stream diffuser end. As a result, the ANC structure can be made integral with the air handler unit, AHU, which incorporates the fan or blower.

It is an object of this invention to provide a low noise air handler unit.

It is another object of this invention to integrate an active noise cancellation system into an air handler.

It is a further object of this invention to reduce the size impact of active noise control devices by better integration of active noise control systems with blowers.

It is an additional object of this invention to utilize underutilized space within a conventional AHU and thereby minimize the size increase due to ANC integration. These objects and others as will become apparent hereinafter, are accomplished by the present invention.

Basically, the internal fan or blower arrangement of an AHU is reconfigured by discharging directly from the scroll of the blower into a 90° elbow with velocity pressure recovery and expansion taking place in the downstream leg of the elbow. Additionally, the ANC structure is located in the elbow thereby allowing inclusion of the ANC bearing duct within the AHU.

BRIEF DESCRIPTION OF THE DRAWINGS

For a fuller understanding of the present invention, reference should now be made to the following detailed description thereof taken in conjunction with the accompanying drawings wherein.

DESCRIPTION OF THE PREFERRED EMBODIMENTS

Figure 1:
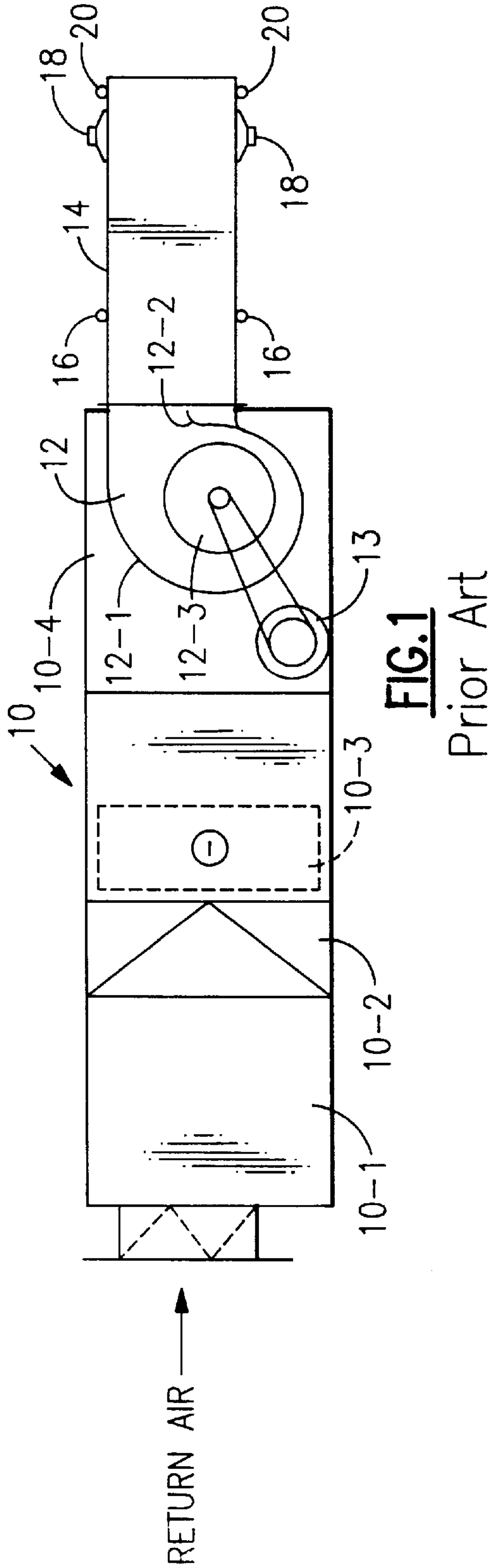
FIG.1 Prior Art
FIG. 1 is a PRIOR ART air handler unit with a horizontal discharge and a conventional duct ANC system located at the outlet.

In FIG. 1, the numeral 10 generally designates a conventional AHU with conventional duct ANC structure located in duct 14 which is connected to the discharge of fan 12. The AHU 10 is typically made up of a plurality of sections and/or subassemblies including mixing box 10-1, filter 10-2, coil 10-3 and fan housing 10-4. Fan 12 has a cutoff 12-2 which defines the actual outlet from scroll 12-1 but, as is conventional, the outlet defined at the cutoff discharges into the larger duct 14. For maximum performance, expansion of the flow is allowed to take place in the duct 14 for a distance equal to three times the diameter of blower 12-3. In that distance the turbulence associated with the fan discharge diminishes along with the associated difficulties with locating sensing microphones 16 in a region where considerable flow generated noise is present. A typical duct ANC system can require a ten foot spacing to accommodate the input noise sensing microphones(s) 16, the noise canceling speaker(s) 18 and the error sensing microphone(s) 20.

In operation, blower 12-3 is driven by motor 13 thereby drawing return and makeup air into the AHU, through a heat exchanger defined by coil 10-3 to heat or cool the air and delivering the resultant conditioned air from scroll 12-1 into duct 14. The fan noises are sensed by microphone(s) 16 and through circuitry (not illustrated) speaker(s) 18 is driven to produce a signal to cancel the fan noise. Microphone(s) 20 sense the result of the noise cancellation by speaker(s) 18 and through circuitry (not illustrated) the output of speaker (s) 18 is corrected.

Figure 2:
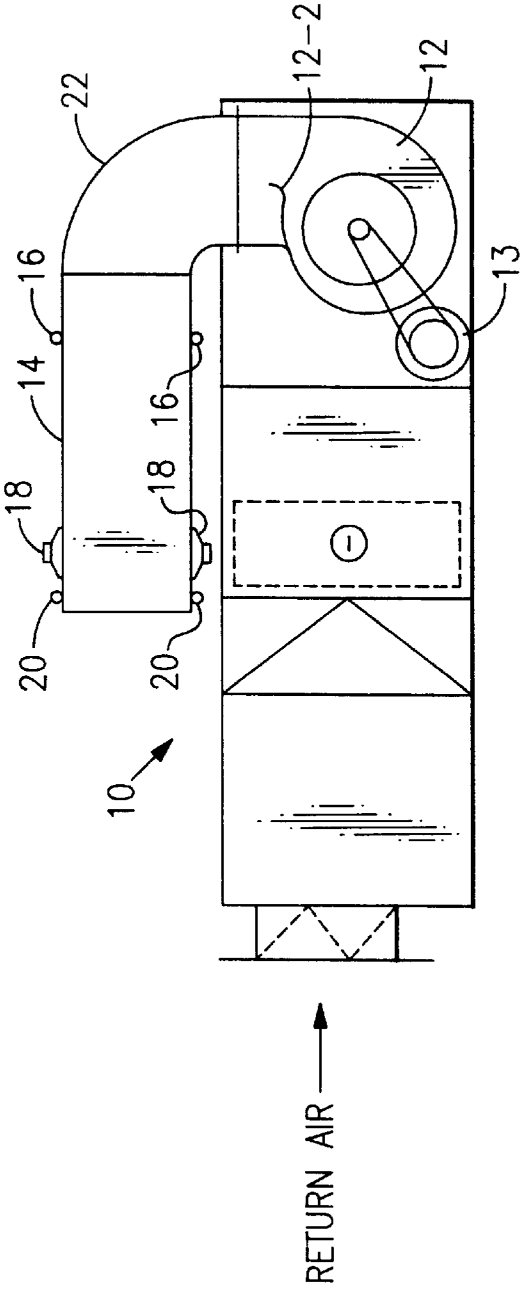
FIG.2 Prior Art
FIG. 2 is a PRIOR ART air handler with a vertical discharge and a 90° elbow connecting the outlet with a conventional duct ANC system.

As noted, the duct ANC system adds ten feet, or so, to the FIG. 1 device. Referring now to FIG. 2, fan 12 of the FIG. 1 device is repositioned to provide a top discharge and 90° elbow 22 is located between blower 12 and duct 14 which employs a conventional ANC system. As compared to the FIG. 1 embodiment, the FIG. 2 embodiment eliminates the length added by duct 14 but requires an additional height clearance to accommodate elbow 22 and the duct 14 above AHU 10. Otherwise, the FIG. 2 device would operate the same as the FIG. 1 device.

Figure 3:
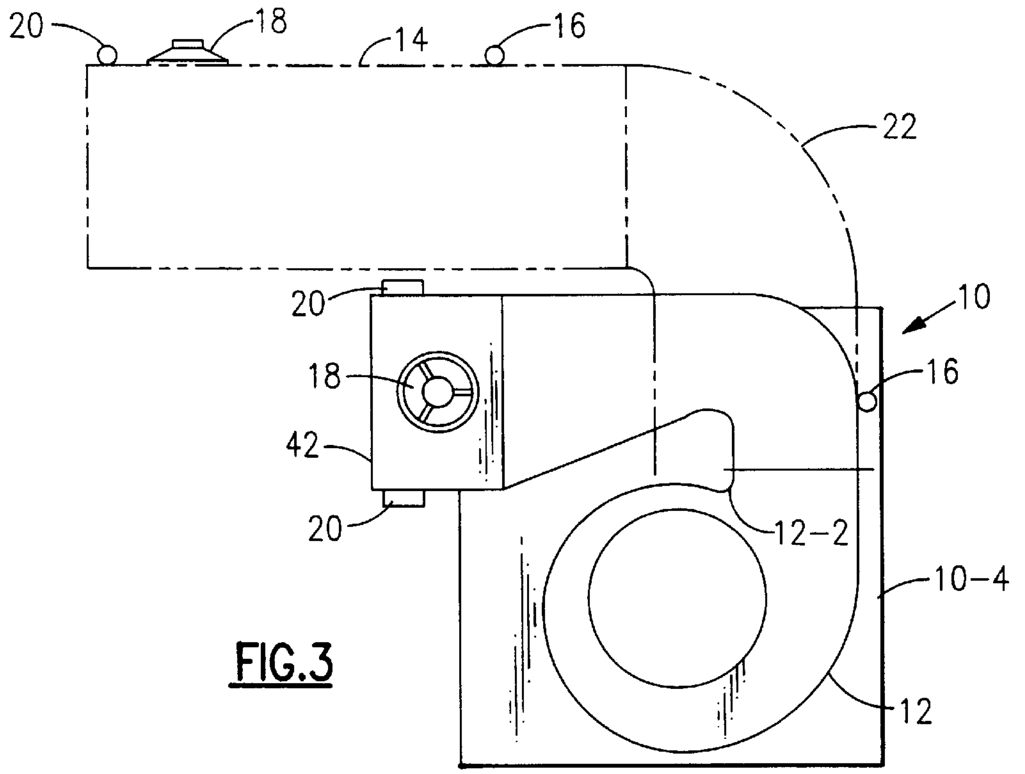
FIG. 3 is a comparison of the blower and ANC elbow of the present invention to the FIG. 2 device so as to show the relative compactness.
Figure 4:
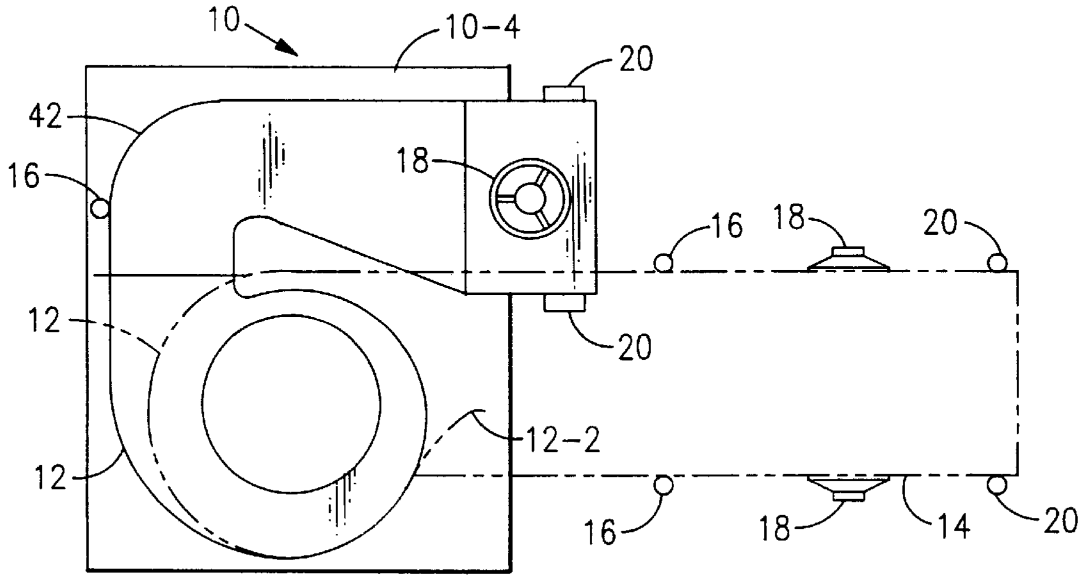
FIG. 4 is a comparison of the blower and ANC elbow of the present invention with a horizontal discharge from the elbow to the FIG. 1 device so as to show the relative compactness.

It should be clear that adding conventional duct ANC structure to a conventional AHU unit requires significant additional space. The present invention, as illustrated in FIGS. 3 though 7, reduces the additional space requirements by using the blower discharge at the cutoff 12-2 to define the cross sectional size of the inlet leg of 90° elbow 42. Since the inlet leg of elbow 42 is smaller in cross section than the inlet of elbow 22, the resultant bend is smaller. Additionally, the present invention reduces the cross section in the bend of elbow 42 leading to the downstream leg of the elbow 42 before expanding it at least to the cross section of the entrance of inlet leg and usually expanding it farther. The present invention also incorporates the ANC system into elbow 42 which requires that the downstream leg of elbow 42 be longer than the inlet leg since the inlet leg is kept as short as possible to minimize the added length/height to the AHU 10. Referring specifically to FIG. 3, it is readily apparent that incorporating the ANC system into elbow 42 which is connected to blower 12 at the outlet defined by cutoff 12-2 provides a significant space saving over the use of elbow 22 and conventional ANC containing duct 14. Referring now to FIG. 4, with blower 12 reoriented to provide a vertical discharge into ANC elbow 42, it will be seen that a horizontal discharge results but requires much less space than ANC containing duct 14.

The locating of the ANC structure into elbow 42 depends upon locating the sensing microphone(s) 16 at or near the blower outlet where flow noises due to turbulence normally preclude the placement of the sensing microphone(s) 16. The placement of sensing microphone(s) 16 in the region of the blower outlet is possible through the use of the turbulence shields which are the subject of commonly assigned U.S. patent application Ser. No. 08/699,674 filed Aug. 30, 1996 and now U.S. Pat. No. 5,808,243, and U.S. patent application Ser. No. 08/871,020 filed Jun. 6, 1997. Accordingly, ANC elbow 42 can be integrated into AHU 10/fan 12.

With the blower 12 located in fan housing 10-4 which is located at one end of the AHU 10, there are four possible fan discharges namely horizontal discharge, top and bottom, and vertical discharge, forward and rearward. The blower 12 is, conventionally, appropriately oriented for the desired discharge. The ANC elbow 42 can be located within the fan housing portion 10-4 of AHU 10 with blower 12, or may be external to the fan housing portion 10-4 of AHU 10 and only secured thereto at the blower outlet defined by cutoff 12-2. The ANC elbow 42 changes the fan outlet direction by 90° and blower 12 would be repositioned accordingly when ANC elbow 42 is employed.

Figure 5:
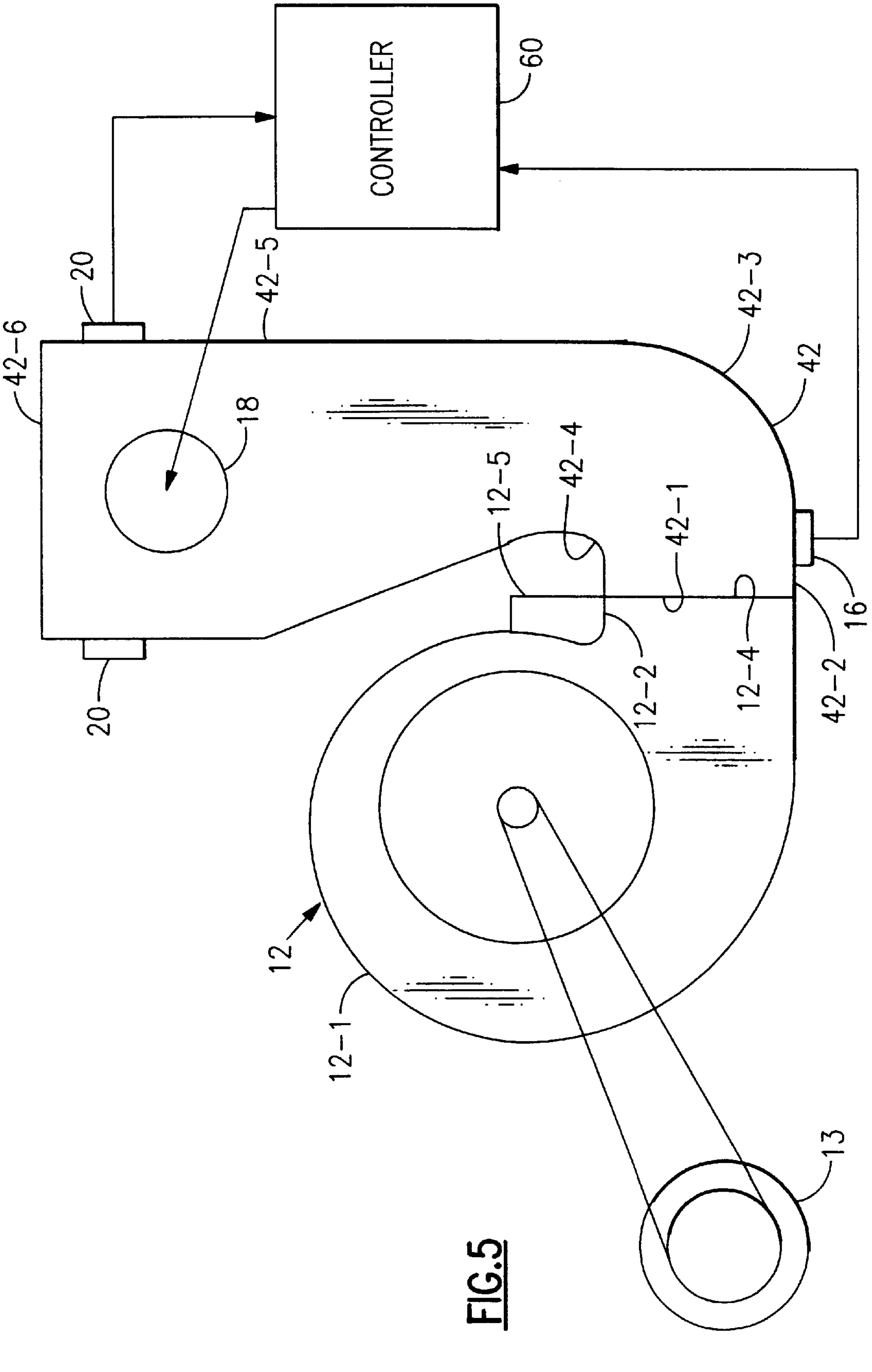
FIG. 5 is a side view of a fan and the ANC elbow of the present invention with a vertical discharge connected to an ANC controller.

FIG. 5 illustrates a blower 12 having a bottom horizontal discharge. As is conventional, blower 12 has a cutoff 12-2 which defines the actual outlet 12-4 of scroll 12-1. Conventionally, the outlet of fan 12 is considered to include portion 12-5 which, together with outlet 12-4, constitutes a cross section corresponding to the cross sectional area of the duct 14 of FIGS. 1–4. The inlet 42-1 of elbow 42 corresponds to outlet 12-4. Inlet leg 42-2 of elbow 42 is very short and blends into 90° bend 42-3. The 90° bend 42-3 converges in the downstream direction to a throat 42-4 having a cross sectional area less than that of inlet 42-1. Downstream of throat 42-4, leg 42-5 diverges so that the outlet 42-6 of elbow 42 is at least as large as inlet 42-1, and usually larger. Outlet 42-6 will, upon installation, be connected to a duct which expands in cross section to that corresponding to duct 14 of FIGS. 1–4. As is conventional, input noise sensing microphone(s) 16, speaker(s) 18 and error sensing microphone(s) 20 are connected to controller 60 which, responsive to the fan noise sensed by microphone(s) 16 causes speaker 18 to be driven to produce a noise canceling signal. Error sensing microphone(s) 20 sense the result of the noise canceling achieved by speaker 18 and controller 60 corrects the driving of speaker 18 responsive thereto.

Figure 6:
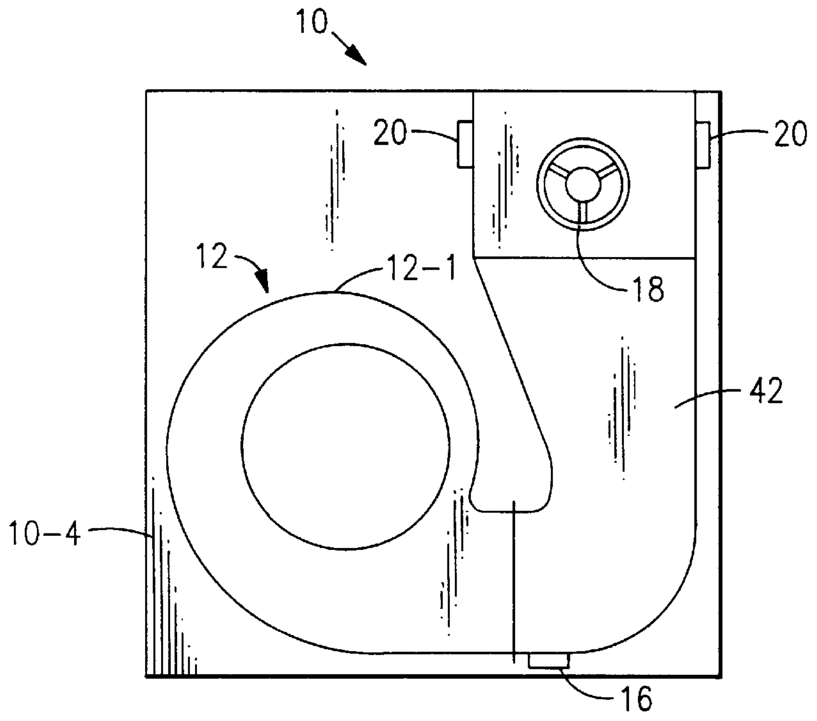
FIG. 6 is the same as FIG. 5 except that the fan and ANC elbow are located within the AHU housing and the circuitry and motor are not shown.
Figure 7:
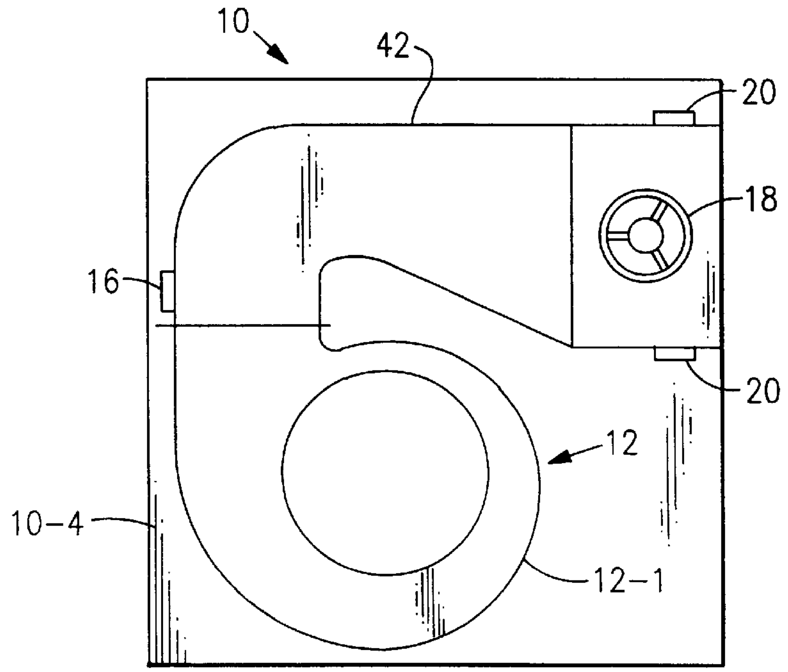
FIG. 7 is a side view of a fan and ANC elbow located within the AHU housing an having a horizontal discharge.

The incorporation of ANC structure into elbow 42 further reduces the size/dimensional requirements as compared to conventional duct ANC systems. As noted above, sensing microphone 16 is located proximate inlet 42-1 pursuant to the teachings of U.S. Pat. No. 5,808,243 and Ser. No. 08/871,020, which are hereby incorporated by reference, and essentially avoids the turbulence flow associated noise. Noise canceling loudspeaker 18 is located in leg 42-5, usually in the fall cross sectional area downstream of throat 42-4. However, if the leg 42-5 is long enough, the loudspeaker 18 may be located in the expanding section. Error microphone(s) 20 are located near, and preferably opposite or a little downstream of loudspeaker 18. FIG. 6 is identical to FIG. 5 except that fan 12 is illustrated within fan housing 10-4 of AHU 10 and the motor 13, controller 60 and circuitry have been omitted. ANC elbow 42 is illustrated as located inside of fan housing 10-4 of AHU 10, but it may be located wholly or partially outside of AHU 10 if necessary or desired. FIG. 7 shows the fan 12 and ANC elbow 42 repositioned relative to the FIG. 6 position so as to provide a horizontal rather than a vertical discharge otherwise the structure and operation would be the same.

Although preferred embodiments of the present invention have been described and illustrated, other changes will occur to those skilled in the art. For example, although the elbow 42 is illustrated as a single member, one or more of the legs may be made separate from the bend portion. Also, although the fan and ANC elbow are indicated as part of the AHU, they may be separately made, sold and/or used. It is therefore intended that the scope of the present invention is to be limited only by the scope of the appended claims.

What is claimed is:

1. An active noise control system comprising:

an elbow having a first leg and a second leg with said first leg having an inlet and said second leg having an outlet with a flow path therebetween;

means for sensing noise in said first leg;

means for producing a noise canceling signal in said second leg.

2. The noise control system of claim 1 further including means for sensing noise in said second leg.

3. The noise control system of claim 1 wherein said first leg is much shorter than said second leg.

4. The noise control system of claim 1 wherein said elbow further includes a bend portion located between said first and second legs having a converging portion and said second leg has a diverging portion.

5. The noise control system of claim 4 wherein said outlet is at least as large as said inlet.

6. The noise control system of claim 1 further including an air handler unit including a fan including a scroll having a cutoff and an outlet partially defined by said cutoff with said inlet corresponding to and connected to said outlet of said scroll.

7. The noise control system of claim 1 further including a fan having a scroll having a cutoff and with an outlet partially defined by said cutoff with said inlet corresponding to and connected to said outlet of said scroll.

8. The noise control system of claim 7 further including means for sensing noise in said second leg.

9. The noise control system of claim 7 wherein said first leg is much shorter than said second leg.

10. The noise control system of claim 7 wherein said elbow further includes a bend portion located between said first and second legs having a converging portion and said second leg has a diverging portion.

11. The noise control system of claim 10 wherein said outlet of said second leg is at least as large as said inlet.

12. An air handler unit including a fan having a scroll, a cutoff and a scroll outlet partially defined by said cutoff, the improvement comprising an active noise control system connected to said scroll outlet and comprising:

an elbow having a first leg and a second leg with said first leg having an inlet corresponding to said scroll outlet and said second leg having an outlet with a flow path therebetween;

means for sensing noise in said first leg;

means for producing a noise canceling signal in said second leg.

13. The noise control system of claim 12 further including means for sensing noise in said second leg.

14. The noise control system of claim 12 wherein said first leg is much shorter than said second leg.

15. The noise control system of claim 12 wherein said elbow further includes a bend portion located between said first and second legs having a converging portion and said second leg has a diverging portion.

16. The noise control system of claim 15 wherein said outlet of said second leg is at least as large as said inlet.

* * * * *